(12) United States Patent
Bagheri et al.

(10) Patent No.: US 9,206,095 B2
(45) Date of Patent: *Dec. 8, 2015

(54) LOW VISCOSITY OLIGOMER OIL PRODUCT, PROCESS AND COMPOSITION

(71) Applicant: INEOS USA LLC, Lisle, IL (US)

(72) Inventors: Vahid Bagheri, League City, TX (US); Lionel D. Moore, Pearland, TX (US); Peter M. DiGiacinto, Seabrook, TX (US); Michel Sanchezrivas, Arquennes (BE)

(73) Assignee: INEOS USA LLC, Lisle, IL (US)

( * ) Notice: Subject to any disclaimer, the term of this patent is extended or adjusted under 35 U.S.C. 154(b) by 226 days.

This patent is subject to a terminal disclaimer.

(21) Appl. No.: 13/852,793

(22) Filed: Mar. 28, 2013

(65) Prior Publication Data
US 2013/0225459 A1    Aug. 29, 2013

Related U.S. Application Data

(63) Continuation-in-part of application No. 12/734,830, filed as application No. PCT/US2008/013157 on Nov. 26, 2008, now Pat. No. 8,455,416.

(60) Provisional application No. 61/004,741, filed on Nov. 29, 2007, provisional application No. 61/008,378, filed on Dec. 20, 2007.

(51) Int. Cl.
*C07C 2/02* (2006.01)
*C10L 1/16* (2006.01)
(Continued)

(52) U.S. Cl.
CPC . *C07C 11/02* (2013.01); *C07C 2/20* (2013.01); *C10G 45/00* (2013.01); *C10G 50/02* (2013.01); *C10M 105/04* (2013.01); *C10M 107/10* (2013.01); *C10G 2300/1088* (2013.01); *C10G 2300/1092* (2013.01); *C10G 2400/10* (2013.01); *C10M 2203/1006* (2013.01); *C10M 2203/1025* (2013.01); *C10M 2205/006* (2013.01); *C10M 2205/022* (2013.01); *C10M 2205/024* (2013.01); *C10M 2205/0285* (2013.01); *C10M 2205/06* (2013.01); *C10M 2205/22* (2013.01); *C10M 2207/026* (2013.01); *C10M 2207/028* (2013.01); *C10M 2207/2835* (2013.01); *C10M 2209/084* (2013.01); *C10M 2215/06* (2013.01); *C10M 2215/223* (2013.01); *C10M 2215/28* (2013.01); *C10M 2219/02* (2013.01);
(Continued)

(58) Field of Classification Search
CPC .................................................... C10M 107/10
USPC .................................. 508/100, 591; 585/525
See application file for complete search history.

(56) References Cited

U.S. PATENT DOCUMENTS 4,172,855 A * 10/1979 Shubkin et al. ................. 585/16
5,087,788 A    2/1992 Wu
(Continued)

FOREIGN PATENT DOCUMENTS

EP    0406536    1/1991

*Primary Examiner* — Prem C Singh
*Assistant Examiner* — Francis C Campanell
(74) *Attorney, Agent, or Firm* — Ineos USA LLC

(57) ABSTRACT

The present invention relates to a low viscosity lubricant process, product, and composition characterized by low Noack volatility, low pour point, useful low temperature viscometrics, and high viscosity index and more particularly concerns a PAO composition having a kinetic viscosity at 100° C. in the range of about 4 cSt.

19 Claims, 4 Drawing Sheets

(51) Int. Cl.
  *C10M 169/04*   (2006.01)
  *C07C 11/02*   (2006.01)
  *C10M 105/04*   (2006.01)
  *C07C 2/20*   (2006.01)
  *C10G 50/02*   (2006.01)
  *C10M 107/10*   (2006.01)
  *C10G 45/00*   (2006.01)

(52) U.S. Cl.
  CPC .. *C10M 2219/024* (2013.01); *C10M 2219/046* (2013.01); *C10M 2223/04* (2013.01); *C10M 2223/045* (2013.01); *C10N 2220/021* (2013.01); *C10N 2220/022* (2013.01); *C10N 2220/023* (2013.01); *C10N 2220/025* (2013.01); *C10N 2220/028* (2013.01); *C10N 2230/02* (2013.01); *C10N 2230/10* (2013.01); *C10N 2230/74* (2013.01); *C10N 2240/04* (2013.01); *C10N 2240/10* (2013.01); *C10N 2240/102* (2013.01); *C10N 2240/12* (2013.01); *C10N 2240/30* (2013.01); *C10N 2260/02* (2013.01); *C10N 2270/00* (2013.01)

(56) References Cited

U.S. PATENT DOCUMENTS 5,498,815 A    3/1996  Schaerfl, Jr.
6,824,671 B2  11/2004  Goze \* cited by examiner

LOW VISCOSITY OLIGOMER OIL PRODUCT, PROCESS AND COMPOSITION

This application is a divisional application of U.S. application Ser. No. 12/734,830, filed Oct. 25, 2010, which is a nationalization under 35 U.S.C. 371 of International Patent Application No. PCT/US2008/013157, filed Nov. 26, 2008, which claims benefit of priority to U.S. Provisional Application No. 61/004,741, filed Nov. 29, 2007 and U.S. Provisional Application No. 61/008,378, filed Dec. 20, 2007.

FIELD OF THE INVENTION

Oligomers of alpha olefins (also known as linear alpha olefins or vinyl olefins), and their use in the formulation of synthetic and semi-synthetic lubricants is known in the art.

Traditionally, the alpha olefin oligomers that have proved useful as synthetic base fluids are prepared mainly from linear terminal olefins containing about 8-14 carbon atoms such as 1-octene, 1-decene, 1-dodecene, 1-tetradecene and mixtures thereof. One of the most widely used alpha olefins is 1-decene which can be used alone or in a mixture with other alpha olefins. When linear alpha olefins are employed, the oligomer products comprise mixtures which include varying amounts of dimer, trimer, tetramer, pentamer and higher oligomers. The oligomer products are typically hydrogenated to improve thermal and oxidative stability and must be further fractionated to be most useful. Hydrogenated and fractionated oligomer products are known for their superior performance, long use-life, low volatility, low pour points, and high viscosity indexes. This makes them premier base stocks for many lubricant applications.

BACKGROUND OF THE INVENTION

Numerous conventional methods exist for producing polyalphaolefin (PAO) compositions. However, these methods suffer from inefficiencies and there remains a need for more effective methods for making polyalphaolefins. Also there remains a need for polyalphaolefins (PAOs) having improved properties.

In a conventional polyalphaolefin process, product kinematic viscosities can be adjusted by either removing or adding higher or lower oligomers to provide a composition having the desired viscosity for a particular application. Viscosities in the range of 2 to 100 cSt, 2 to 10 cSt, and 4 cSt at 100° C. are useful.

A particularly large market exists for synthetic lubricant base stocks having kinematic viscosity of 4 cSt at 100° C. especially if this property is combined with low Noack volatility, low pour point, useful low temperature viscosity, and high viscosity index. The 4 cSt PAO made in the decene oligomerization provides a useful balance of properties. Unfortunately, the 4 cSt material (mainly decene trimer or C30) must be distilled from a complex oligomer mixture and is generally accompanied by a heavier co-product.

It is desirable to produce 4 cSt compositions having similar or better properties compared to decene-based oils from feed stocks other than decene—due to the limited decene supply. It is also desirable to produce the aforesaid 4 cSt composition selectively and without any co-products.

The present invention relates to a low viscosity polyalphaolefin (PAO) composition characterized by low Noack volatility, low pour point, inventive low temperature viscometrics, high viscosity index, and low sludge forming tendencies and more particularly concerns a PAO composition having a kinetic viscosity at 100° C. in the range of about 4 cSt. The invention also relates to an improved process for the selective production of the aforesaid composition without formation of any heavier co-products. Furthermore, the invention also relates to an improved process for the selective production of the aforesaid composition without formation of any heavier co-products comprising a very high (co)dimer content with minimal amounts of trimer and heavier oligomers using a BF3 catalyst along with a promoter system containing at least an ester and an embodiment consisting of an alcohol and an ester system in reaction involving at least one alpha olefin with at least one vinylidene olefin (a branched alpha olefin with alkyl substitution at the 2 carbon position).

DESCRIPTION OF THE PRIOR ART

Figure 1:
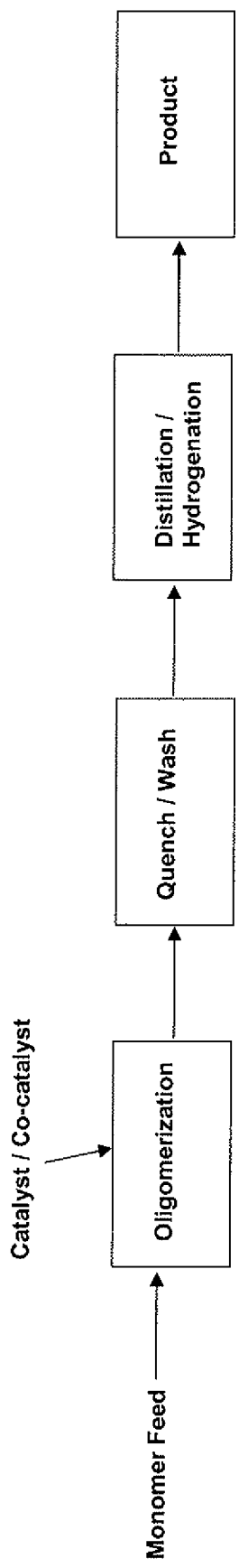
FIG. 1 schematically illustrates the process diagram of the lubricant of the present invention.
Figure 2:
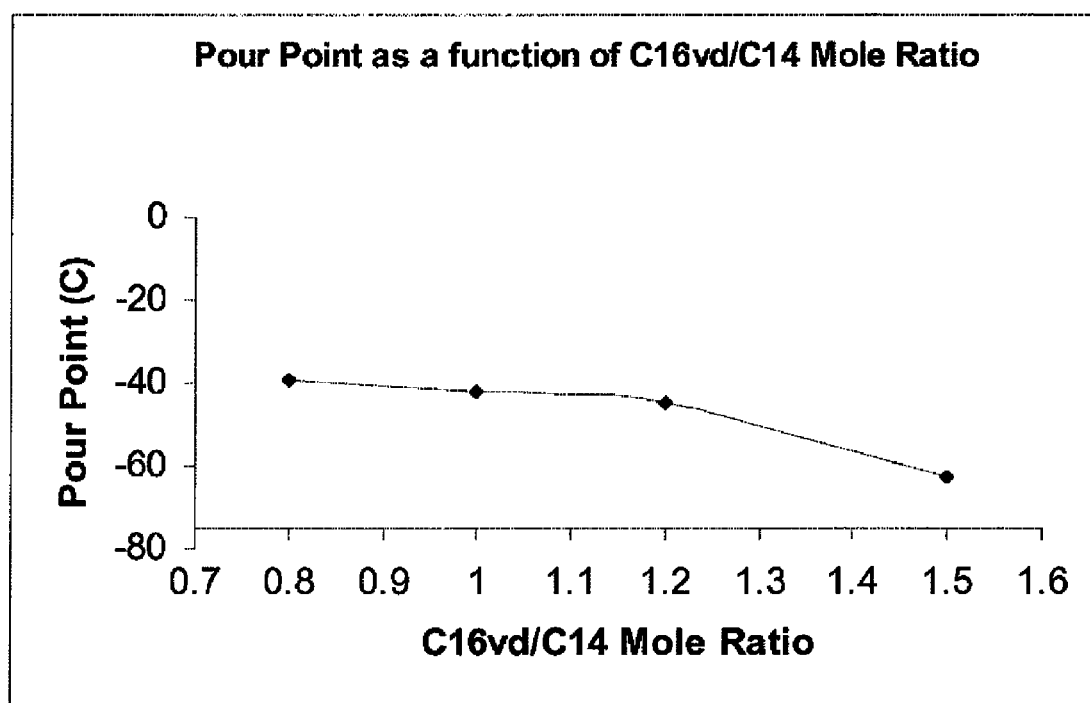
FIG. 2 schematically illustrates the Pour Point versus the composition of the present invention.
Figure 3:
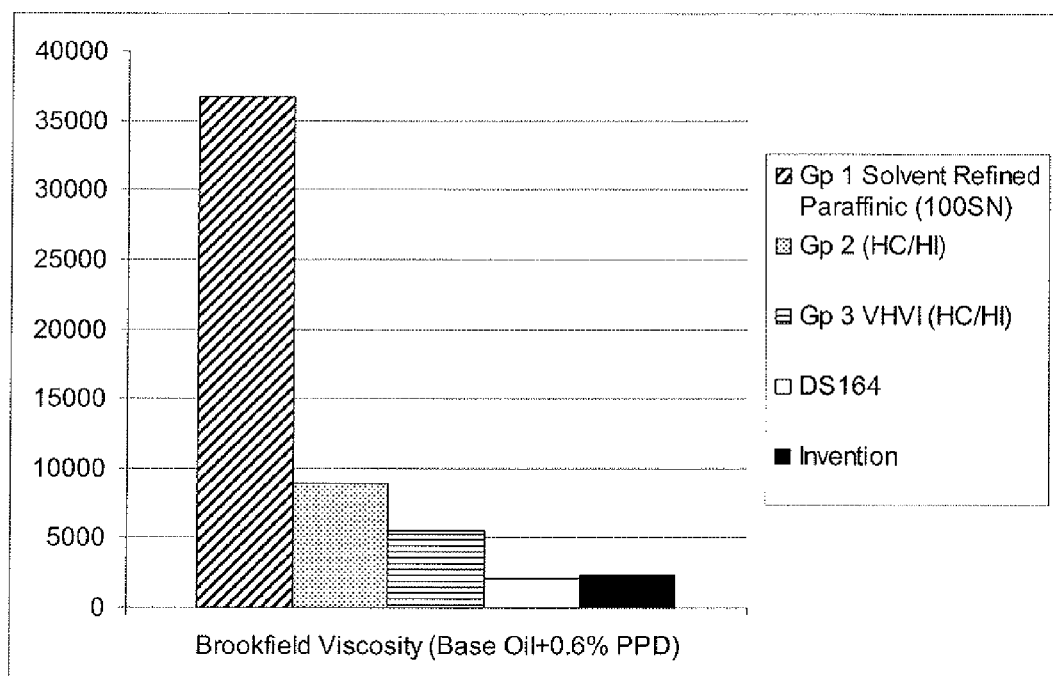
FIG. 3 schematically illustrates the Brookfield viscosity of the present invention.
Figure 4:
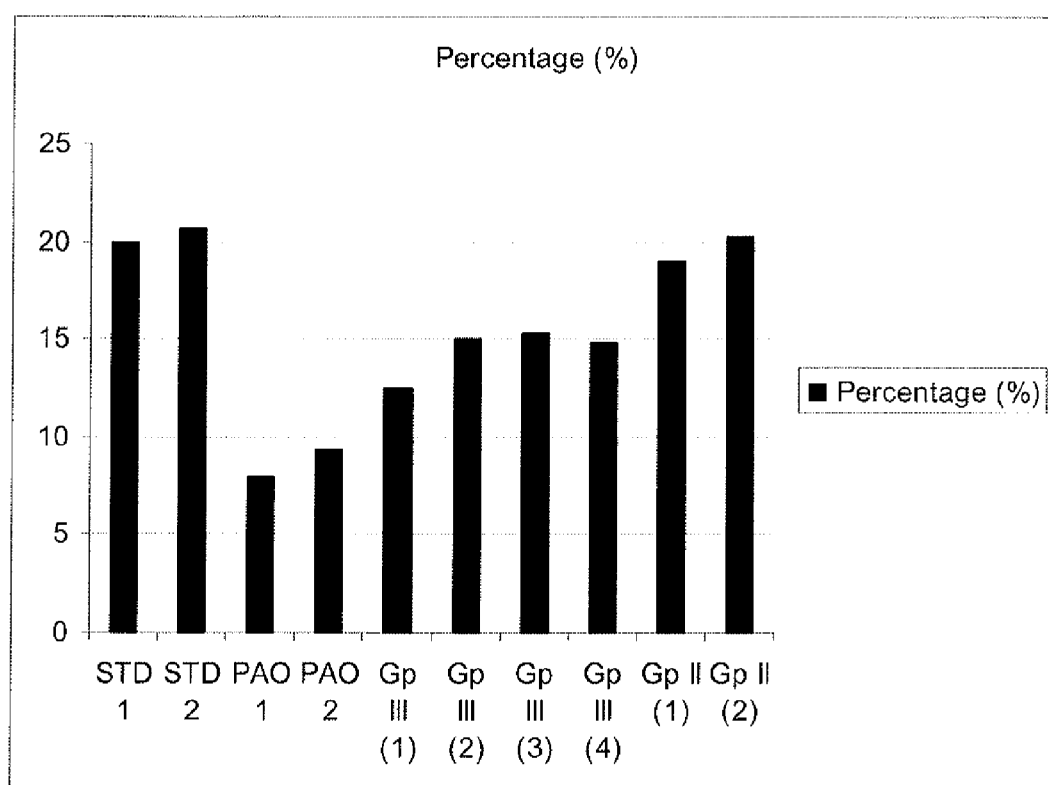
FIG. 4 schematically illustrates the Tertiary Carbons by NMP GASPE C13 of the present invention.

Oligomers of alpha olefins (PAO) and their use as synthetic lubricants are well known. The following patents illustrate but a few of the many methods described for making PAO oligomers. See for example, U.S. Pat. Nos. 3,682,823; 3,763,244; 3,769,363; 3,780,123; 3,798,284; 3,884,988; 3,097,924; 3,997,621; 4,045,507; and 4,045,508.

In many applications it is preferred that the oligomer have a low viscosity, for example, below about 5 cSt and below about 4 cSt at 100° C. These low viscosity fluids are especially useful in energy saving applications such as engine lubricating oil to minimize friction and thus improve fuel economy. Used either alone or as blends with mineral oil they can, for example, provide lubricating oils with viscosities which qualify as SAE 0W 30 or SAE 5W30 crankcase oils.

In the past, useful oligomers having desired properties have been made by oligomerizing 1-decene using a Friedel-Crafts catalyst such as BF3 with a promoter such as an alcohol. However, 1-decene is in limited supply because it is a co-product made together with a broad range of other alpha olefins. It is therefore beneficial to provide more flexibility in making synthetic base stocks using a broader range of alpha olefins while producing oligomers having substantially similar viscometric properties. Additionally, a problem associated with making oligomer oils from 1-decene or other alpha olefins is that the oligomer product mix usually must be fractionated into different portions to obtain oils of a given viscosity (e.g. 2, 4, 6, or 8 cSt at 100° C.). The commercial production provides an oligomer product mix which, when fractionated, produces the relative amounts of each viscosity product which correspond to market demand. Therefore, necessarily, an excess of one product is produced in order to obtain the needed amount of the other.

Shubkin, et al., U.S. Pat. No. 4,172,855 discloses a process for making a low viscosity oligomer comprising dimerizing a C6-C12 alpha olefin, in which the resultant dimer is reacted with C6-18 alpha olefin in the presence of a Friedel-Crafts catalyst, distilling out the volatile components and hydrogenating the residual product. The fluid however has a Pour Point of −45° C. containing a measurable amount of the heavier oligomers component of C42-48 reported at 7.26%.

Schaerfl et al., U.S. Pat. No. 5,284,988 discloses a process comprising (a) isomerizing at least a portion of a vinylidene olefin feed in the presence of an isomerization catalyst to form an intermediate which contains tri-substituted olefin and (b) reacting said intermediate and at least one vinyl olefin in the presence of a catalyst. This requires an additional isomerization step; also, the extent of heavier undesired oligomers C42+ is still too high and reported at 6.5%.

Schaerfl et al U.S. Pat. No. 5,498,815 discloses a multi-step process for making a synthetic oil requiring an initial step of (a) reacting a vinylidene olefin in the presence of a catalyst to form an intermediate mixture which contains at least about 50 weight percent dimer of the vinylidene olefin. This adds complexity by requiring an initial dimerization of the vinylidene to at least about 50 weight percent dimer.

Theriot et al U.S. Pat. No. 5,650,548 discloses a process by contacting an alpha olefin with a catalyst system comprising $BF_3$, a protic promoter, an organic sulfone, sulfoxide, carbonate, thiocarbonate, or sulfonate producing oligomer containing as much as 50% or more dimer of the alpha olefin. EP 0 467 345 A2 discloses a process for making dimers of alpha olefins with a catalyst comprising $BF_3$ and an alcohol alkoxylate. U.S. Pat. No. 3,997,621 discloses a process for oligomerization of alpha olefins that maximizes the yield of trimer as the dominant product catalyzed by $BF_3$ in combination with an alcohol and an ester, further, U.S. Pat. No. 6,824,671 discloses a process for oligomerization of alpha olefins containing a mixture of about 50 to 80 wt % 1-decene and about 20 to 50 wt % 1-dodecene in a continuous mode by using $BF_3$ with an alcohol/ester promoter system also maximizing the trimer yield. These are among many examples of catalyst modifications aimed at controlling degree of oligomerization in prior art with focus on alpha olefins while we describe a highly selective process involving combination of vinylidene olefins and alpha olefins.

SUMMARY OF THE INVENTION

The present invention relates to a 4 cSt polyalphaolefin (PAO) composition characterized by low Noack volatility, low pour point, inventive low temperature viscometrics, high viscosity index, and low sludge forming properties made selectively by the reaction of C16 vinylidene (2-n-hexyl-1-decene) with 1-tetradecene using a $BF_3$ catalyst along with promoter system containing of at least an ester or two promoters consisting of an alcohol and an ester system. The aforesaid composition comprises the mole ratios C16 vinylidene/1-tertadecene in the range of about 1 to 2 and most preferably at 1.5. The invention also relates to an improved process for the selective production of the aforesaid composition without formation of any heavier co-products comprising a very high (co)dimer content with minimal amounts of trimer and heavier oligomers using a BF3 catalyst along with a promoter system containing at least an ester and most preferably consisting of an alcohol and an ester system. The hydrogenated composition of this invention has a viscosity at 100° C. of about 4 cSt, a Noack volatility weight loss of less than 15%, a Viscosity Index of greater 120, a Pour Point lower than –50° C., and a viscosity at –40° C. of less than 3000 cSt.

DETAILED DESCRIPTION OF THE INVENTION

The present invention describes a process for the production of lubricant comprising:
(a) reacting first alpha olefin in the presence of a first catalyst to form vinylidene olefin;
(b) reacting said vinylidene olefin with second alpha olefin in the presence of $BF_3$ catalyst and a promoter system comprising at least one aprotic promoter;
(c) removing residual unreacted monomers;
(d) hydrogenating said bottom product to produce lubricating oil composition.

As an embodiment of the present process the first alpha olefin used to form vinylidene olefin selected from the group consisting of linear $C_{4-20}$ 1-olefin and combinations thereof. The vinylidene olefin comprises a vinylidene content of greater than 70%.

The process of the present invention provides wherein said first catalyst comprises an alkyl aluminum catalyst, a metallocene catalyst, a bulky ligand late transition metal catalyst, and combinations thereof. An embodiment of the present process provides first catalyst comprising trialkyl aluminum catalyst. The first catalyst comprises metallocene catalyst selected from the metal Periodic Group IVB.

As an embodiment of the present invention the second alpha olefin can be selected from the group consisting of linear $C_{4-20}$ 1-olefin and combinations thereof.

The promoter system of the invention comprises at least one aprotic promoter combined with at least one protic promoter. As an embodiment the protic promoter is selected from $C_1$-$C_{20}$ alcohols. The alcohol comprises selection from 1-propanol or 1-butanol. A further embodiment of the present invention provides said promoter system comprises at least one aprotic promoter without the protic promoter. As an embodiment of the present invention, the aprotic promoter comprises selection from the group consisting of aldehydes, anhydrides, ketones, organic esters, ethers and combinations thereof. A further embodiment of the present invention, the aprotic promoter comprises an organic ester selected from the group consisting of $C_1$-$C_{10}$ alkyl acetates and combinations thereof. The aprotic promoter can comprise an alkyl acetate. As an embodiment, the alkyl acetate can comprise n-butyl acetate.

The present invention contemplates removing residual unreacted monomers comprising distillation.

The vinylidene olefin of the present invention comprises dimerization of 1-octene to a C16 vinylidene. The vinylidene olefin can comprise purity of at least 80%. Also, said vinylidene olefin comprises reacting C16 vinylidene with 1-tetradecene (C14). The 1-tetradecene (C14) comprises a linear terminal purity of at least 70%. The vinylidene olefin comprises purity of at least 80%.

The lubricant oil composition of the present invention comprises about 4 cSt viscosity at 100° C., a Noack volatility weight loss of less than 15%, a Viscosity Index of greater than 120, a Pour Point lower than –50° C., and viscosity at –40° C. of less than 3000 cSt. As an embodiment, the lubricant oil composition comprises production without heavier co-product. As a further embodiment, the lubricant oil composition comprises a mole ratio of C16 vinylidene to 1-tetradecene of between about 1 to about 2. The lubricant oil composition can comprise a mole ratio of C16 vinylidene to 1-tetradecene of about 1.5.

As an embodiment, the process of claim 1 wherein the lubricant mixed with fluid selected from the group consisting of synthetic fluid, mineral oil, dispersant, anti-oxidant, anti-wear agent, anti-foam agent, corrosion inhibitor, detergent, seal-swell agent, viscosity improver and combinations thereof.

A further embodiment of the present invention process provides for the production of lubricant comprising:
(e) reacting first alpha olefin in the presence of a first catalyst to form
(f) vinylidene olefin;
(g) reacting said vinylidene olefin with second alpha olefin in the presence of $BF_3$ catalyst and a promoter system comprising at least one aprotic promoter;

(h) removing residual unreacted monomers;
(i) hydrogenating at least a portion of said bottom product; and
(j) recovering hydrogenated fluid.

The unhydrogenated fluid of the invention can be useful in a variety of derivative type applications in which the olefin group can be functionalized to form a heteroatom functionality selected from the group consisting of nitrogen, oxygen, sulfur, halogen, and combinations thereof.

Useful PAO viscosities are in the range of 2 to 100 cSt and especially 2 to 10 cSt and most particularly for a 4 cSt viscosity at 100° C. It is an object of this invention to produce a 4 cSt compositions having similar or better properties comparing to decene-based oil from other feed stocks as decene supply is limited. It is also an objective of this invention to produce the aforesaid 4 cSt selectively and without any co-products. A particularly large market exist for synthetic lubricant base stocks having a kinematic viscosity of 4 cSt at 100° C. especially if it is combined with low Noack volatility, low pour point, useful low temperature viscosity, and high viscosity index. The present invention relates to a 4 cSt polyalphaolefin (PAO) composition characterized by low Noack volatility, low pour point, inventive low temperature viscometrics, and high viscosity index made selectively by the reaction of C16 vinylidene (2-n-hexyl-1-decene) with 1-tetradecene using a $BF_3$ catalyst along with promoter system containing of at least an ester or a two promoter system consisting of an alcohol and an ester. The C16 vinylidene (C16vd) is produced by dimerization of 1-octene having vinylidene purity greater than 70% and is independent of the preparation method or source. The C16vd can be prepared by the methods described in U.S. Pat. No. 5,625,105 and references therein or by the methods described in U.S. Pat. No. 5,087,788, U.S. Pat. No. 4,658,078, or U.S. Pat. No. 6,548,723. In an embodiment, the invention is a 4 cSt polyalphaolefin (PAO) composition characterized by low Noack volatility, low pour point, inventive low temperature viscometrics, and high viscosity index made selectively by the reaction of C16 vinylidene with 1-tertadecene. The aforesaid composition is arrived when the mole ratios C16 vinylidene/1-tetradecene is in the range of about 1 to 2, about 1.5. Further, the composition of this invention has a viscosity at 100° C. of about 4 cSt, a Noack volatility weight loss of less than 15%, a Viscosity Index of greater 120, a Pour Point lower than −50° C., and a viscosity at −40° C. of less than 3000 cSt.

Another object of the present invention also relates to an improved process for the selective production of the aforesaid composition without formation of any heavier co-products comprising a very high (co)dimer content with minimal amounts of trimer and heavier oligomers using a $BF_3$ catalyst along with a promoter system containing at least an ester, and an embodiment consisting of an alcohol and an ester system. The desired 4 cSt composition of this invention is produced as a single product without any heavier co-products once residual and unreacted monomer fraction is removed requiring no further fractionation. Further, the content of trimer and higher oligomer fractions of the present invention is kept below 5%.

Another embodiment of the current invention is to produce 4 cSt synthetic base fluid with a low contribution to sludge and inventive oxidation stability over the prior art.

It is desirable to produce a 4 cSt composition having similar or better properties compared to decene-based oil from other feed stocks as the decene supply is limited. It is also desirable to produce the aforesaid 4 cSt selectively and without any co-products. Extensive comparative testing comparing the current invention to commercially available products has been performed.

As used herein, the term "about" modifying any amount refers to the variation in that amount encountered in real world conditions of producing lubricant, lubricant oil compositions or producing their precursors, e.g., in the lab, pilot plant, or production facility. For example, an amount of an ingredient employed in a mixture when modified by "about" includes the variation and degree of care typically employed in measuring in a lubricant, lubricant oil compositions or producing their precursors in production plant or lab. For example, the amount of a component of a product when modified by "about" includes the variation between batches lubricant, lubricant oil compositions or producing their precursors in production plant or lab and the variation inherent in the analytical method. Whether or not modified by "about," the amounts include equivalents to those amounts. Any quantity stated herein and modified by "about" can also be employed in the present invention as the amount not modified by "about."

ADDITIONAL DISCLOSURE OF THE PRESENT INVENTION

The present invention addresses increasing shortage in traditional 4 cSt PAO used in the formulation of high performance oils.

The present invention comprises using alphaolefins feedstock to generate a complementary 4 cSt PAO that comprises critical properties similar or better than exisiting commercial product.

Interchangeability with commercial product under ATIEL Read Across procedure.
Similar or better Properties/Performance than existing commercial products:
  VI and Noack Performance
  Cold Crank Viscosity
  Tertiary Hydrogens (Oxidative stability)
  Thermally Stable
  Flash Point
  Additive solubility
  Traction coefficient
  Additives Response
Similar or better Properties/Performance than existing commercial products:
  VI and Noack Performance
  Cold Crank Viscosity
  Tertiary Hydrogens (Oxidative stability)
  Thermally Stable
  Flash Point
  Additive solubility
  Traction coefficient
  Additives Response
The present invention has been developed on 'bench scale' and 'semi-industrial' facilities.

The present invention provides extensive lab scale work focused on optimizing properties for a 4 cSt product to meet or exceed DS 164 industry standard PAO.

Bench performance testing undertaken for comparative look against DS 164, the present invention shows equivalent or superior performance:
Neat base oils and formulated oils (gear, compressor, ATF, PCMO)
Results from lab scale to 100× and 1000× the lab scale of the present invention work in semi-industrial scale equipment.

Bench Scale Product Properties
The Present Invention General Properties

Semi-Industrial Embodiments of Present Invention

Scale up factor 100× to 1000× versus bench scale
Production of 2.5 MTons
Ranges of operating parameters explored at this scale Embodiments of the Present Invention Present invention offers inventive properties/performance to DS 164 in many respects including Pour Point.
Present invention provides the following benefits:
 Fuel Economy
 Energy Efficiency
 Drain Intervals
Present invention can be replacement for DS 164 volumes
Present invention provides more flexibility to lubricant customers to source 4 cSt PAO.
Values and Availability of the Present Invention
The present invention provides a method to lift availability constraints on decene based PAO.
The present invention provides the desirable characteristics of traditional 4 cSt PAO as a minimum.
As an embodiment of the present invention raw material LAO comprises PAO feedstock.
The present invention process can be adapted for standard PAO units, 25 ktpa to mid 40 ktpa (target order of magnitude).

EXAMPLES

Commercially produced 1-tetradecene (C14) from INEOS Oligomers was used; other versions of 1-tetradecene can be used. The C16 vinylidene (C16vd) is produced by dimerization of 1-octene having vinylidene purity greater than 70% and is independent of the preparation method or source.

Example 1

A 1-gallon Parr reactor equipped with jacketed heating and internal cooling was charged with 515.0 g 1-tetradecene and 885.0 of C16 vinylidene (89% vinylidene olefin, 8% internal olefin, and 3% trisubstituted olefin by H NMR), 1.4 g 1-butanol, and 1.4 g butyl acetate and was taken to 30° C. with stirring. Boron trifluoride was introduced and it was adjusted to a steady state pressure of 20 psi; an immediate exotherm to 43° C. was observed which was controlled within 3 minutes. The reaction was stirred for 30 minutes. The oligomerization reaction was also conducted in manner that portion or all of the reactants are added slowly to the Parr reactor for a better control of the exotherm; it can also be performed in a continuous mode employing 2-5 continuous stirred tank reactors (CST) in series or parallel. The reaction mixture quenched with 400 ml 8% NaOH and washed with distilled water. Removal of unreacted and volatile fluids under reduced pressure (200° C., 0.1 mmHg) resulted in isolation of 1244.6 g of a clear fluid which was hydrogenated under a set of standard hydrogenation conditions (at 170° C., 400 psi hydrogen, using Ni on Kieselguhr catalyst) to produce a synthetic basestock having the following properties:

TABLE 1

| Analysis | Method | Units | Properties |
|---|---|---|---|
| KV 100° C. | ASTM D-445 | $mm^2/S$ | 3.93 |
| KV 40° C. | ASTM D-445 | $mm^2/S$ | 17.3 |
| VI | ASTM D-2270 | — | 124 |
| KV −40° C. | ASTM D-445 | $mm^2/S$ | 2435 |
| Pour Point | ASTM D-97 | ° C. | −63 |
| Flash Point | ASTM D-92 | ° C. | 208 |
| Noack | DIN 51581 | % wt | 13.6 |
| Appearance | Visual | | clear |
| Brookfield Visc.@−40° C. | IP 267 | mPaS | 2160 |
| Refractive Index @20° C. | ASTM D-1218 | — | 1.4554 |
| CCS-30° C. | ASTM D5293 | mPa · S | <700 |
| CCS −35° C. | ASTM D5293 | mPa · S | 1220 |
| TAN | ASTM D-974 | mgKOH/g | 0.003 |
| Density 15° C. | ASTM D-4052 | g/ml | 0.8198 |
| Bromine number | IP-129 | g/100 g | 0.2 |

The table above shows that once the residual unreacted monomers are removed, the resultant PAO has an inventive balance of viscometric properties (i.e. properties matching many of those of conventional decene-based 4 cSt PAOs) and can be used as a straight run single recipe 4 cSt fluid without further distillation. It is a 4 cSt fluid with useful Viscosity Index, low Noack volatility, and inventive Pour Point.

Oligomer composition of the above PAO by GC showed the following composition:
 C24: 1.9 area %
 C28-C32: 95.0 area %
 C42-C48 (trimer and higher): 3.1 area %

Minimizing the heavier trimer and higher fractions (C42-C48) to about less than 5% is a key feature of this invention that brings about above mentioned desired properties eliminating the need for further distillation and combines useful viscometric properties including very low Pour Point into a single recipe 4 cSt PAO in which no heavier co-products are formed.

GC Conditions:
 Column: 15 m×0.53 mm id×0.1 µm film, DB-1
 Oven Temperature Program: 90° C. to 330° C. at 8°/min. Hold 330° C. for 10 min.
 Injector Temperature: Off
 Injector Type: On-column
 Column Head Pressure: 3 psig to 15 psig at 0.5 psig/min. Hold 15 psig for 16 min.
 Carrier Gas: Helium
 Detector Type: Flame Ionization (FID)
 Detector Temp: 300° C.
 Column Flow: 7 ml/min (90° C./3 psig)
 Column Flow: 21 ml/min (300° C./15 psig)
 Auxiliary Flow: 15 ml/min
 Attenuation×Range: 7×1
 Sample Injected: 1.0 µl (fused silica needle)
 Instrument: HP 5890 series II Gas Chromatograph
 Sample Preparation:
 Samples were prepared for analysis by weighing 40 mg PAO into a 4-dram vial. One milliliter of internal standard solution (1.2 mg/ml nC15 in n-heptane) was added to the samples vial and the mixture diluted with 10 ml n-heptane. Response factor of 1.0 was used in all sample calculations. Normalization of results to 100% may be required.
 Retention Times:
 Component retention times are as follows:
 Dimer: 10-15 minutes
 Trimer: 15-21 minutes
 Tetramer: 21-26 minutes
 Pentamer: 26-29 minutes
 Hexamer+: 29-33 minutes Structural analysis of this fluid by GASPE NMR method showed a significantly lower tertiary carbon content than a decene based commercially available equal viscosity fluid (like Durasyn 164 from INEOS): 7.9% vs. 9.1%. It is known in the art that the least oxidatively stable part of the molecule are tertiary carbon positions, that is, the point where there are branches in the carbon chains. This makes the PAO fluid of this invention especially useful for applications requiring or benefiting from improved oxidative stability.

Gated Spin Echo (GASPE) Analysis:

GASPE (gated spin echo) is an NMR technique that uses interrupted decoupling to determine the percentage of primary, secondary, tertiary, and quaternary carbon atoms present in a molecule. In a typical experiment, after exciting $^{13}C$ nuclei for a specified period, proton decoupling is switched off briefly. Quaternary C's are unaffected but CH, CH2, and CH3 peaks oscillate up and down at different rates.

Several spectra are acquired with carefully selected periods of interrupted decoupling, plus one spectrum with full decoupling. Some spectra have all peaks positive, others have CH, CH2, and/or CH3 peaks negative. The spectra are added together in predefined ratios to give pure C, CH, CH2, and CH3 subspectra. Subspectra are integrated to give the carbon type distribution directly.

Procedure:

The procedure used in this experiment is based on the published work of McKenna et. al. (McKenna, S. T., Casserino, M., and Ratliff, K., "Comparing the Tertiary Carbon Content of PAOs and Mineral Oils", presented at STLE Annual Meeting, May 23, 2002). See also Cookson, D. J., and Smith, B. E., "Improved Methods for Assignment of Multiplicity in $^{13}C$ NMR Spectroscopy with Application to the Analysis of Mixtures", *Org. Magn. Reson.*, 16, 111-6 (1981); Cookson, D. J., and Smith, B. E., "Determination of Carbon C, CH, $CH_2$, and $CH_3$ Group Abundances in Liquids Derived from Petroleum and Coal Using Selected Multiplet $^{13}C$ NMR Spectroscopy", *Fuel*, 62, 34-8 (1983); Cookson, D. J., and Smith, B. E., "Quantitative Estimation of $CH_n$, Group Abundances in Fossil Fuel Materials Using $^{13}C$ NMR Methods", *Fuel*, 62, 986-8 (1983); Snape, C. E., "Comments on the Application of Spin-Echo $^{13}C$ NMR Methods to Fossil Fuel-Derived Materials", *Fuel*, 62, 988-9 (1983); Gallacher, J., Snape, C. E., Dennison, P. R., Bales, J. R., and Holder, K. A., "Elucidation of the Nature of Naphtheno-Aromatic Groups in Heavy Petroleum Fractions by Carbon-13 NMR and Catalytic Dehydrogenation", *Fuel*, 70, 1266-70 (1991); Sarpal, A. S., Kapur, G. S., Chopra, A., Jain, S. K., Srivastava, S. P., and Bhatnagar, A. K., "Hydrocarbon Characterization of Hydrocracked Base Stocks by One- and Two-Dimensional NMR Spectroscopy", *Fuel*, 75, 483-90 (1996); Montanari, L., Montani, E., Corno, C., and Fattori, S., "NMR Molecular Characterization of Lubricating Base Oils: Correlation with Their Performance", *Appl. Magn. Reson.*, 14, 345-56 (1998); and Sahoo, S. K., Pandey, D. C., and Singh, I. D., "Studies on the Optimal Hydrocarbon Structure in Next Generation Mineral Base Oils", *Int. Symp. Fuels Lubr., Symp. Pap.*, 2, 273-8 (2000).

Examples 2-4

Mole ratios of C16/C14 examples provide that the Mole ratios were optimized to obtain PAOs with enhanced viscometric properties; high C14 character in the product adversely impacts Pour Point (high Pour Point). Table below shows examples highlighting impact of C16vd/C14 mole ratios on Pour Point properties of resultant fluids under similar conditions:

TABLE 2

| Examples | C16vd/C14 Mole Ratio | Pour Point° C. |
|---|---|---|
| 1 | 1.5 | −63 |
| 2 | 1.2 | −45 |
| 3 | 1.0 | −42 |
| 4 | 0.8 | −39 |

Examples 5

The 1 gallon oligomerization Parr reactor was charged under an inert N2 atmosphere with 515.0 g 1-tetradecene (INEOS C14), 885.0 g C16 vinylidene (89% vinylidene olefin, 8% internal olefin, and 3% trisubstituted olefin by H NMR), 2.8 g butyl acetate and was taken to 30° C. with stirring. Boron trifluoride was introduced and it was adjusted to a steady state pressure of 20 psi; an immediate exotherm to 38° C. was observed which was controlled within 3 minutes by the action of chiller and brought back to 30° C. The reaction was stirred at this temperature for 30 minutes, excess BF3 was expelled through the caustic scrubber and the reaction medium was further purged for 15 minutes with N2. The crude reaction mixture was quenched with 400 ml 8% NaOH and the separated organic phased was further washed with distilled water. Removal of unreacted and volatile fluids under reduced pressure (200° C., 0.1 mmHg) resulted in isolation of 1092.2 g of a clear fluid which was hydrogenated under a set of standard hydrogenation conditions (at 170° C., 400 psi hydrogen, using Ni on Kieselguhr catalyst) to produce a synthetic basestock having the following properties:

TABLE 3

| Analysis | Method | Units | Fluid of the INVENTION |
|---|---|---|---|
| KV 100° C. | ASTM D-445 | mm$^2$/S | 3.91 |
| KV 40° C. | ASTM D-445 | mm$^2$/S | 17.3 |
| VI | ASTM D-2270 | — | 121 |
| KV −40° C. | ASTM D-445 | m$^2$/S | 2434 |
| Pour Point | ASTM D-97 | ° C. | −57 |

Table above shows that the resultant PAO has an inventive balance of viscometric properties and can be used as a straight run single recipe 4 cSt fluid without further distillation.

Oligomer composition of the above PAO by GC showed the following composition:

C28-C32: 97.8 area %

C42-C48 (trimer and higher): 2.0 area %

Comparative Example (Not the Claimed Invention)

Above oligomerization experiment was conducted employing conventional recipe using 1-butanol as the only promoter system with BF3 (with exclusion of butyl acetate as the only exception otherwise similar reaction conditions). The resultant fluid had the following properties after the standard hydrogenation:

TABLE 4

| Analysis | Method | Units | Properties |
|---|---|---|---|
| KV 100° C. | ASTM D-445 | mm$^2$/S | 4.20 |
| KV 40° C. | ASTM D-445 | mm$^2$/S | 18.9 |
| VI | ASTM D-2270 | — | 128 |
| KV −40° C. | ASTM D-445 | mm$^2$/S | 2936 |
| Pour Point | ASTM D-97 | ° C. | −45 |
| Noack | DIN 51587 | % wt | 13.9 |

The product of the above comparative example has significantly higher Pour Point (−45° C. vs. −63° C.) and is considered off-specification when compared with commercially available 4 cSt decene-based PAO, such as INEOS Durasyn 164. Other differences include both the 100° C. viscosity (Durasyn 164 specification maximum is 4.1 cSt) and the −40° C. viscosity (Durasyn 164 specification maximum is 2800 cSt). Additionally, composition of this comparative example fluid by GC showed a significantly higher percentage of heavier oligomers (trimer and higher):

C24: 1.4 area %
C28-C32: 89.6 area %
C42-C48 (trimer and higher): 9.0 area %

Higher Pour Point and higher viscosities (at 100° C. and at −40° C. respectively) of this fluid stem in part from the higher percentage of trimer and heavier oligomers of the comparative example which lacks the higher selectivity of the inventive process when butyl acetate was employed as a secondary modifier in addition to 1-butanol.

Example 6

The Low Sludge Formation of the Product of the Present Invention Compared to Fluid with Higher Trimer Content The thermal stability of the neat fluid of the invention, having a kinematic viscosity at 100° C. of 3.93 cSt, a 40° C. viscosity of 17.26 cSt, and a C42-C48 (trimer and higher) content of 2.9% was evaluated in the ASTM D2070 test (Cincinnati Milacron Thermal Stability Test, Procedure A) along with a fluid, prepared by the procedure of the comparative example detailed above, having a kinematic viscosity at 100° C. of 4.20 cSt, a 40° C. viscosity of 18.79 cSt, and a C42-C48 (trimer and higher) content of 7.0%

In the Cincinnati Milacron test, copper and steel rods in contact with the test fluids are evaluated for appearance and weight loss after 168 hours at 135° C. Sludge is evaluated by filtering the test oil and weighing the residue according to the established procedure. In the comparison below, the fluid of the invention has lower sludge than the comparative C14/C16 fluid by a factor of greater than six.

TABLE 5

| | Method | Fluid of the Invention | COMPARATIVE FLUID |
|---|---|---|---|
| Viscosity at 100 C | ASTM D-445 | 3.93 | 4.20 |
| Viscosity at 100 C | ASTM D-445 | 17.26 | 18.79 |
| Percent C42-C48 (trimer and higher) | GC | 2.9% | 7.0% |
| Cincinnati Milacron Thermal Stability, Procedure A (ASTM D-2070) | | | |
| Relative Total Sludge (mg) | | 1 | 6.3 |
| Cu Rod Rating | | 2 | 6 |
| Fe Rod Rating | | 3 | 2 |

Example 7

The Oxidative Stability of the Fluid of the Present Invention Compared to Hydrogenated 1-Decene-Based 4 cSt Polyalphaolefin (Durasyn 164) Commercial Comparator Hydrogenated oligomers of alpha olefins are susceptible to oxidative deterioration especially when exposed to high temperatures in the presence of iron or other catalytic metals. Oxidation, if not controlled, can contribute to the formation of corrosive acid products, sludge, and varnish that may interfere with the proper functioning of a fully formulated lubricant containing the oligomers. While it is common to include antioxidants to fully formulated lubricants to mitigate oxidation, it is of some value to confirm that the starting hydrogenated alpha olefin oligomers are inherently stable. To that end, the product of the invention was tested in several industry standard oxidation stability tests along with a hydrogenated 1-decene-based 4 cSt polyalphaolefin (Durasyn 164) as a comparator.

The oxidation stability of the fluid of the invention and its comparator were measured using the rotary pressure vessel oxidation test (RPVOT; ASTM D 2272). This test method utilizes an oxygen-pressured vessel to evaluate the oxidation stability of fluids in the presence of water and a copper catalyst coil at 150° C. The fluid of the invention has an oxidation induction time that is 9% longer than that of the 4 cSt decene PAO. An oil giving a longer oxidation induction time is generally considered to be more resistant to oxidation.

The Thin Film Oxygen Uptake Test (TFOUT) was conducted according to the test method specified in ASTM D 4742. The test utilizes a rotating pressure vessel in a hot oil bath. The vessel is charged with oxygen to 90 psig and run until the oxygen pressure decreases. The longer the test runs (in minutes), the better the oxidative resistance of the fluid. The fluid of the invention has an oxidation induction time that is 13% longer than that for the 4 cSt decene PAO.

Institute of Petroleum test method 48 (the IP-48) was next used to evaluate the oxidative stability of the fluid of the invention versus 4 cSt decene PAO.

In this test, air is bubbled through the fluid which is kept at high temperature. The viscosity of the end-of-test sample is compared to that of a reference sample which has the exact same composition but is bubbled through with nitrogen. The net viscosity increase (expressed as a percentage increase) is an indication for the oxidation stability of a lubricant. The lower the viscosity increase, the better. The fluid of the invention shows a viscosity ratio (viscosity of used oil/viscosity of new oil) of 2.98 versus 3.48 for the 4 cSt decene PAO.

TABLE 6

| TEST | METHOD | MEASURED | INVENTION | 4 cSt C10 PAO |
|---|---|---|---|---|
| Oxidation Stability (RPVOT) | ASTM D2272 | Relative Oxidation Induction Time, min | 109% | 100% |
| Oxidation Stability (TFOUT) | ASTM D4742 | Relative Induction Time, min | 113% | 100% |
| Oxidation Stability | IP 48 | | | |
| Viscosity Ratio (Used/New) | | | 2.98 | 3.48 |
| Δ Ramsbottom Residue (Used vs. New) | | | 0.08 | 0.09 |
| Evaporative Loss | | wt. % | 16.26 | 17 |

In all of the tests above, the fluid of the invention is equivalent to or directionally superior to the 4 cSt decene PAO comparator.

Example 8

Motor Oils

The 4 cSt fluid of this invention, having low viscosities as measured at 100° C. and −40 viscosity respectively combined with a useful viscosity index and a low Pour Point (all as previously defined) can be used in many lubricant applications.

It is anticipated that the synthetic fluids of the current invention will be used wherever hydrogenated 1-decene oligomers of similar viscosity are used. Applications include, but are not limited to, hydraulic fluids for earth- and water-moving equipment, automotive crankcase oils, heavy duty diesel oils, automatic transmission fluids, continuously variable transmission fluids, and industrial and automotive gear oils, compressor/turbine oils and particularly applications benefiting from energy saving features inherent in low viscosity fluids. Several demonstration formulations were devised to illustrate the suitability of the fluid of the invention for a number of formulation types.

Passenger Car Motor Oils

The synthetic fluids made by the present invention are ideally suited for use as components of full synthetic and/or semi-synthetic lubricating oils used in internal combustion engines. The fluid of the invention can be used as the entire base lubricant or can be blended with other lubricating oils including Group I, II, or III mineral oils, GTL (gas to liquid) oils, synthetic ester oils (e.g. di-2-ethylhexyl adipate, trimethylolpropane tripelargonate, etc.), alkyl naphthalene oils (e.g. di-dodecylnapthalene, di-tetradecylnapthalene, etc.) and the like. The lubricating oils used in internal combustion engines are typically formulated to contain conventional lubricating oil additives such as calcium aryl sulfonates, overbased calcium sulfonates, calcium or barium phenates, overbased magnesium alkylbenzene sulfonates, zinc dialkyldithiophosphates, VI improvers (e.g. ethylene-propylene copolymers, polyalkylmethacrylates, etc.), ashless dispersants (e.g. polyisobutylenesuccinimides of tetraethylene pentamine, polyisobutylenephenol-formaldehyde-tetraethylene pentamine Mannich condensation products, etc.), pour point depressants, friction modifiers, rust inhibitors, demulsifiers, oil soluble antioxidants (e.g. hinder phenols or alkylated diphenyl amines), various sulfurized components, and foam inhibitors (anti-foams).

Proprietary combinations of such additives, called additive packages, are tailored for specific base oils and applications, and are commercially available from several sources including Lubrizol, Infineum, and Afton Corporations. Viscosity Index (VI) improvers are available from these and other suppliers.

The fluid of the invention can be used to formulate 0W and 5W viscosity grade passenger car motor oils that are desirable for their energy conserving qualities (see SAE paper 871273, 4$^{th}$ International Pacific Conference, Melbourne, Austalia, 1987).

Example 8A

Passenger Car Demonstration Oil

The following 0W-30 and 0W-40 full and part-synthetic passenger car motor oils were formulated containing the fluid of the INVENTION.

TABLE 7

0W-30 and 0W-40 PCMO

| | Full-Synthetic 0W-30 | | Part-Synthetic 0W-40 | |
|---|---|---|---|---|
| ADDITIVE | il A | Oil B | Oil C | il D |
| Additive Package[1], Wt % | 14.2 | 14.2 | 12.5 | 12.5 |
| Group III base oil, 6 cSt[2], Wt % | — | — | 20.0 | 20.0 |
| C$_{10}$ PAO 6 cSt[3], Wt % | 51.8 | 51.8 | — | — |
| C$_{10}$ PAO 4 cSt[4], Wt % | 20.0 | — | 48.5 | — |
| INVENTION 3.9 cSt, Wt % | — | 20.0 | — | 48.5 |
| Viscosity Modifier[5], Wt % | 4.0 | 4.0 | 9.0 | 9.0 |
| Ester[6], Wt % | 10.0 | 10.0 | 10.0 | 10.0 |
| KV @ 100° C. (cSt) | 10.9 | 10.8 | 13.4 | 13.2 |
| KV @ 40° C. (cSt) | 64.9 | 65.0 | 76.9 | 78.7 |
| Viscosity Index | 159 | 158 | 179 | 168 |
| Cold Cranking Simulator Viscosity, −35° C. (cP) | 5290 | 5250 | 4930 | 5010 |
| Noack Volatility (% wt loss) | 7.6 | 7.4 | 8.6 | 8.8 |

[1]Commercial dispersant/inhibitor package from Lubrizol
[2]Hydrogenated 1-decene polyalphaolefin from INEOS; 5.97 cSt at 100° C.
[3]Hydrogenated 1-decene polyalphaolefin from INEOS; 3.93 cSt at 100° C.
[4]Group III mineral oil from SK Korea; 6.52 cSt at 100° C., 129 VI, −15° C. pour point
[5]15% m/m solution of hydrogenated polyisoprene polymer in PAO6 from Shell
[6]Hindered ester of Trimethylolpropane from Uniqema

Example 8B

Heavy Duty Diesel Oils—Heavy Duty Diesel Demonstration Oil

The synthetic fluids of the invention are useful for the formulation of heavy duty diesel engine oils. Like passenger car motor oils, heavy duty diesel oils contain several different additive types such as, for example, dispersants, anti-oxidants, anti-wear agents, anti-foams, corrosion inhibitors, detergents, seal swell agents and viscosity index improvers. These types of additives are well known in the art. Some specific examples of additives useful in heavy duty diesel oils include zinc dialkyl-dithiophosphates, calcium aryl sulfonates, overbased calcium aryl sulfonates, barium phenates, hindered alkyl phenols, methylene-bis-dialkyl phenols, high molecular weight alkyl succinimides of ethylene-polyamines such as tetraethylene-polyamine, sulfur-bridged phenols, sulfurized fatty acid esters and amides, silicones and dialkylesters. Proprietary combinations of such additives, which are tailored for specific base oils and applications, are commercially available from several sources including Lubrizol, Infineum, and Afton Corporations. Viscosity Index (VI) improvers are separately available from these and other producers.

The following 5W-40 part-synthetic heavy duty diesel oils were formulated containing the fluid of the invention.

TABLE 8

5W-40 HDDO

| ADDITIVE | Part-Syn 5W-40 | |
|---|---|---|
| | Oil E | Oil F |
| Additive Package[1], Wt % | 20.0 | 20.0 |
| $C_{10}$ PAO 4 cSt[2], Wt % | 6.0 | — |
| Group III base oil, 6 cSt[3], Wt % | 20.0 | 20.0 |
| INVENTION 3.9 cSt, Wt % | — | 46.0 |
| Viscosity Modifier[4], Wt % | 10.0 | 10.0 |
| Ester[5], Wt % | 5.0 | 5.0 |
| KV @ 100° C. (cSt) | 13.7 | 13.3 |
| KV @ 40° C. (cSt) | 82.5 | 83.7 |
| Viscosity Index | 171 | 60 |
| Cold Cranking Simulator Viscosity, −30° C. (cP) | 4390 | 4450 |
| Noack Volatility (% wt loss) | 7.6 | 7.9 |

[1]Commercial dispersant/inhibitor package from Afton
[2]Hydrogenated 1-decene polyalphaolefin from INEOS; 3.93 cSt at 100° C.
[3]Group III mineral oil from SK Korea; 6.52 cSt at 100° C., 129 VI, −15° C. pour point
[4]hydrogenated polyisoprene polymer from Shell
[5]Di-tridecyl adipate from Exxon Example 8C Compressor/Turbine Demonstration Oil The synthetic fluids of the invention can be used in the formulation of compressor oils (together with selected lubricant additives). The preferred compressor oil is typically formulated using the synthetic fluid of the present invention together with a conventional compressor oil additive package. The additives listed below are typically used in such amounts so as to provide their normal attendant functions. The additive package may include, but is not limited to, oxidation inhibitors, additive solubilizers, rust inhibitors/metal passivators, demulsifying agents, and anti-wear agents.

Other base oils are also anticipated.

TABLE 9

ISO 22 Compressor/Turbine Oil

| ADDITIVE | Oil G | Oil H |
|---|---|---|
| Anti-oxidant[1], Wt % | 0.50 | 0.50 |
| Additive package[2], Wt % | 0.87 | 0.87 |

TABLE 9-continued

ISO 22 Compressor/Turbine Oil

| ADDITIVE | Oil G | Oil H |
|---|---|---|
| Seal Swell Agent[3], Wt % | 10.00 | 10.00 |
| Antifoam[4], Wt % | 0.01 | 0.01 |
| $C_{10}$ PAO 6 cSt[5], Wt % | 35.45 | 35.45 |
| $C_{10}$ PAO 4 cSt[6], Wt % | 53.17 | — |
| INVENTION 3.9 cSt, Wt % | — | 53.17 |
| KV @ 40° C. (cSt) | 19.97 | 20.02 |
| KV @ 100° C. (cSt) | 4.40 | 4.43 |
| Viscosity Index | 134 | 135 |
| Pour Point, ° C. | <−62 | <−60 |
| Flash point, ° C. | 210 | 214 |
| Specific Gravity | 0.8314 | 0.8317 |
| Copper Strip Corrosion, ASTM D130 | 1a | 1a |
| Demulsibility, ASTM D1401 | 40/40/0 | 40/40/0 |
| Relative RPVOT Induction Time, min (ASTM D2272) | 100 | 104 |

[1]Commercial alkyl phenol and aryl amine antioxidant from Afton
[2]Commercial performance package containing alkyl phosphonate, aryl amine, aryl triazole, and other components from Afton
[3]Commercial seal swell agent, 3.6 cSt at 100° C., 14.6 cSt at 40° C. from Afton.
[4]Commercial acrylate anti-foamant from Afton.
[5]Hydrogenated 1-decene polyalphaolefin from INEOS; 5.97 cSt at 100° C.
[6]Hydrogenated 1-decene polyalphaolefin from INEOS; 3.93 cSt at 100° C.

Example 8D

Gear Oils

The synthetic fluids of the invention can be used in the formulation of transportation and industrial gear oils. Typical gear oil formulations contain (1) one or more polymeric thickeners such as high viscosity polyalphaolefins, liquid hydrogenated polyisoprenes, polybutenes, high molecular weight acrylate esters, and ethylene-propylene or ethylene-alphaolefin copolymers; (2) low viscosity mineral oils, such as a Group I, II, or III mineral oils, or low viscosity synthetic oils (e.g. di-alkylated naphthalene, or low viscosity polyalphaolefins); and/or, optionally, (3) low viscosity esters, such as monoesters, diesters, polyesters, and (4) an additive package containing anti-oxidants, dispersants, extreme pressure agents, wear inhibitors, corrosion inhibitors, anti-foams and the like.

Commercially available additive packages contain several, and sometimes all, of the types of additives above.

Gear oils can be single grades or multigrades (i.e. meeting SAE viscosity requirements a both high and low temperatures. For instance, a 75W-90 multigrade gear oil would need to have a minimum viscosity at 100° C. of 13.5 cSt and a viscosity of 150,000 cP or less at −40° C.

Example 8E

Gear Demonstration Oil

TABLE 10

ISO 32 Industrial Gear Oil

| ADDITIVE | Oil I | Oil J |
|---|---|---|
| EP Gear Additive Package[1], Wt % | 1.50 | 1.50 |
| eal Swell Agent[2], Wt % | 10.00 | 10.00 |
| Foam Inhibitor[3], Wt % | 0.01 | 0.01 |
| $C_{10}$ PAO, 40 cSt[4], Wt % | 22.12 | 22.12 |

TABLE 10-continued

ISO 32 Industrial Gear Oil

| ADDITIVE | Oil I | Oil J |
|---|---|---|
| $C_{10}$ PAO 4 cSt[5], Wt % | 66.37 | — |
| INVENTION 3.9 cSt, Wt % | — | 66.37 |
| 100° C. Vis, cSt | 6.33 | 6.38 |
| 40° C. Vis, cSt | 31.78 | 32.01 |
| Flash Point, ASTM D-92 | 216 | 214 |
| Relative Timken Failure Load, lbs (ASTM D-2782) | 100 | 113 |
| FZG Load Stage | 11 | 11 |
| Relative FZG Scuffing Load, g (SAE AIR 4978) | 100 | 104 |
| Relative Ryder Gear Load, lb/in | 100 | 103 |
| Copper Strip Corrosion (ASTM D-130) | 1b | 1b |
| Rust Prevention (ASTM D-665B) | Pass | Pass |
| Demulsibility (ASTM D-1401) | 40/40/0 | 40/40/0 |

[1]Commercial EP gear oil package from Afton
[2]Commercial seal swell agent, 3.6 cSt at 100° C., 14.6 cSt at 40° C. from Afton.
[3]Commercial anti-foamant from Afton.
[4]Hydrogenated 1-decene polyalphaolefin from INEOS; 5.97 cSt at 100° C.
[5]Hydrogenated 1-decene polyalphaolefin from INEOS; 3.93 cSt at 100° C.

TABLE 11

75W-90 Transportation Gear Oil

| ADDITIVE | Oil K |
|---|---|
| EP Gear Additive Package[6], Wt % | 7.50 |
| Seal Swell Agent[7], Wt % | 10.00 |
| Viscosity Modifier/Thickener[8], Wt % | 31.00 |
| Pour Point Depressant[9], Wt % | 1.00 |
| INVENTION 3.9 cSt, Wt % | 50.50 |
| Kinematic Viscosity @ 100° C., cSt | 15.3 |
| Brookfield Viscosity @ −40° C., cP | 106,900 |

[6]Commercial EP gear oil package from Afton
[7]Commercial seal swell agent from Afton.
[8]Commercial viscosity modifier from Afton.
[9]Commercial pour point depressant from Afton.

Example 8F

Transmission Fluids

Transmission fluids are used in automobile transmissions, heavy-duty transmissions for buses and military transports, and in the transmissions of other off-road and over-the-road vehicles. Base oils with useful low temperature properties are required to formulate transmission fluids meeting the latest specifications. While it is not absolutely necessary to use synthetic fluids for many transmission fluid applications, synthetic fluids do allow fluids to be formulated with improved low temperature properties, volatility and oxidative stability.

The synthetic fluids of the INVENTION can be used in the formulation of transmission fluids. A demonstration oil was found to have passing overall performance in the MERCON® Aluminum Beaker Oxidation Test.

TABLE 12

Automatic Transmission Fluid Demonstration Oil

| ADDITIVE | Oil L | Oil M |
|---|---|---|
| Additive Package[1], Wt % | 20.08 | 20.08 |
| $C_{10}$ PAO 6 cSt[2], Wt % | 38 | 38 |
| $C_{10}$ PAO 4 cSt[3], Wt % | 41.89 | — |
| INVENTION 3.9 cSt, Wt % | — | 41.89 |
| Red dye[4], Wt % | 0.03 | 0.03 |
| KV @ 40° C., D445 | 26.79 | 26.64 |
| KV @ 100° C., D445 | 5.75 | 5.74 |
| Viscosity Index, D2270 | 165 | 165 |
| Brookfield Viscosity @ −35 C, D5293 | 2510 | 2390 |
| Pour Point, ° C., D97 | <−60 | −57 |
| Flash Point, ° C., D92 | 224 | 226 |
| Density at 15 C, D4052 | 0.8402 | 0.8402 |
| Aluminum Beaker Oxidation Test | | |
| Δ Viscosity at 40 C (EOT, 300 hours) | — | 1.4% |
| Δ Weight Loss (EOT, 300 hours) | — | 3.3% |
| Δ TAN (mg KOH/g, 300 hours) | — | 1.0 |
| Δ FTIR (EOT, 300 hours) | — | 12 |
| Pentane Insolubles, wt % | — | 0.16 |
| Sludge | — | None |
| Al Strip | — | No varnish |

[1]Proprietary additive package meeting Dexron VI requirements
[2]Hydrogenated 1-decene polyalphaolefin from INEOS; 5.97 cSt at 100° C.
[3]Hydrogenated 1-decene polyalphaolefin from INEOS; 3.93 cSt at 100° C.
[4]C.I. Solvent Red 164

What is claimed is:

1. A synthetic fluid composition comprising a hydrogenated reaction product of a vinylidene olefin having a vinylidene content of greater than 70% with a second alpha olefin, excluding 1-decene, in the presence of $BF_3$ catalyst and a promoter system that includes a mixture of at least one aprotic compound with at least one protic compound;
wherein the synthetic fluid composition includes 5 weight percent or less of C42 to C48 components,
wherein the synthetic fluid has a 3.5 to 4.1 cSt viscosity at 100° C., with Noack volatility weight loss of less than 16%, a Viscosity Index of greater than 120, a Pour Point lower than −50° C., and a viscosity at −40° C. of less than 3000 cSt.

2. The synthetic fluid composition of claim 1 wherein the vinylidene olefin is formed by reacting a first alpha olefin, excluding 1-decene, in the presence of a first catalyst.

3. The synthetic fluid composition of claim 1 wherein the synthetic fluid composition has a ⅙ to ½ lower relative sludge rating than a composition made with a single promoter.

4. The synthetic fluid composition of claim 2 wherein first alpha olefin used to form vinylidene olefin is selected from the group consisting of linear $C_{4-20}$ 1-olefin, excluding 1-decene, and combinations thereof.

5. The synthetic fluid composition of claim 2 wherein said first catalyst is selected from the group consisting of an alkyl aluminum catalyst, a metallocene catalyst, a bulky ligand late transition metal catalyst, and combinations thereof.

6. The synthetic fluid composition of claim 5 wherein said first catalyst is a trialkyl aluminum catalyst.

7. The synthetic fluid composition of claim 5 wherein said first catalyst is a metallocene catalyst selected from the metal Periodic Group IVB.

8. The synthetic fluid composition of claim 1 wherein said second alpha olefin is selected from the group consisting of linear $C_{4-20}$ 1-olefin, excluding 1-decene, and combinations thereof.

9. The synthetic fluid composition of claim 1 wherein the protic promoter is selected from $C_1$-$C_{20}$ alcohols.

10. The synthetic fluid composition of claim 9 wherein the alcohol is 1-propanol or 1-butanol.

11. The synthetic fluid composition of claim 1 wherein the aprotic promoter is selected from the group consisting of aldehydes, anhydrides, ketones, organic esters, ethers and combinations thereof.

12. The synthetic fluid composition of claim 1 wherein the aprotic promoter is an organic ester selected from the group consisting of $C_1$-$C_{10}$ alkyl acetates and combinations thereof.

13. The synthetic fluid composition of claim 12 wherein the aprotic promoter is an alkyl acetate.

14. The synthetic fluid composition of claim 13 wherein the alkyl acetate is n-butyl acetate.

15. The synthetic fluid composition of claim 1 wherein said vinylidene olefin is a C16 vinylidene having a purity of at least 80%.

16. The synthetic fluid composition of claim 15 wherein the C16 vinylidene is reacted with 1-tetradecene (C14) having a linear terminal purity of at least 70%.

17. The synthetic fluid composition of claim 16 wherein a mole ratio of C16 vinylidene to 1-tetradecene is about 1 to about 2.

18. The synthetic fluid composition of claim 17 wherein the mole ratio of C16 vinylidene to 1-tetradecene is about 1.5.

19. The synthetic fluid composition of claim 1 wherein the synthetic fluid composition is mixed with a composition selected from the group consisting of other synthetic fluid, mineral oil, dispersant, anti-oxidant, anti-wear agent, anti-foam agent, corrosion inhibitor, detergent, seal-swell agent, viscosity improver and combinations thereof.

* * * * *